United States Patent [19]
Linden et al.

[11] Patent Number: 5,877,180
[45] Date of Patent: Mar. 2, 1999

[54] METHOD FOR TREATING INFLAMMATORY DISEASES WITH $A_{2A}$ ADENOSINE RECEPTOR AGONISTS

[75] Inventors: Joel M. Linden; Gail W. Sullivan, both of Charlottesville, Va.

[73] Assignee: University of Virginia Patent Foundation, Charlottesville, Va.

[21] Appl. No.: 272,821

[22] Filed: Jul. 11, 1994

[51] Int. Cl.⁶ .................................................. A61K 31/52
[52] U.S. Cl. .......................................... 514/266; 514/262
[58] Field of Search ...................................... 514/262, 266

[56] References Cited

U.S. PATENT DOCUMENTS 5,140,015  8/1992  Olsson et al. .
5,278,150  1/1994  Olsson et al. .
5,665,754  9/1997  Feldman et al. .

OTHER PUBLICATIONS

G. W. Sullivan, H.T. Carper and G.L. Mandell, "Specific Type IV Phosphodiesterase Inhibitor Rolipram Combined with Adenosine Reduces Tumor Necrosis Factor–α–Primed Neutrophil Oxidative Activity," *Int. J. Immunopharmac.*, vol. 17, No. 10, pp. 793–803 (1995).

*Primary Examiner*—William R. A. Jarvis
*Attorney, Agent, or Firm*—Schwegman, Lundberg, Woessner, and Kluth, P.A.

[57] ABSTRACT

Agonists of $A_{2a}$ adenosine receptors are effective for the treatment of inflammatory diseases.

9 Claims, 4 Drawing Sheets

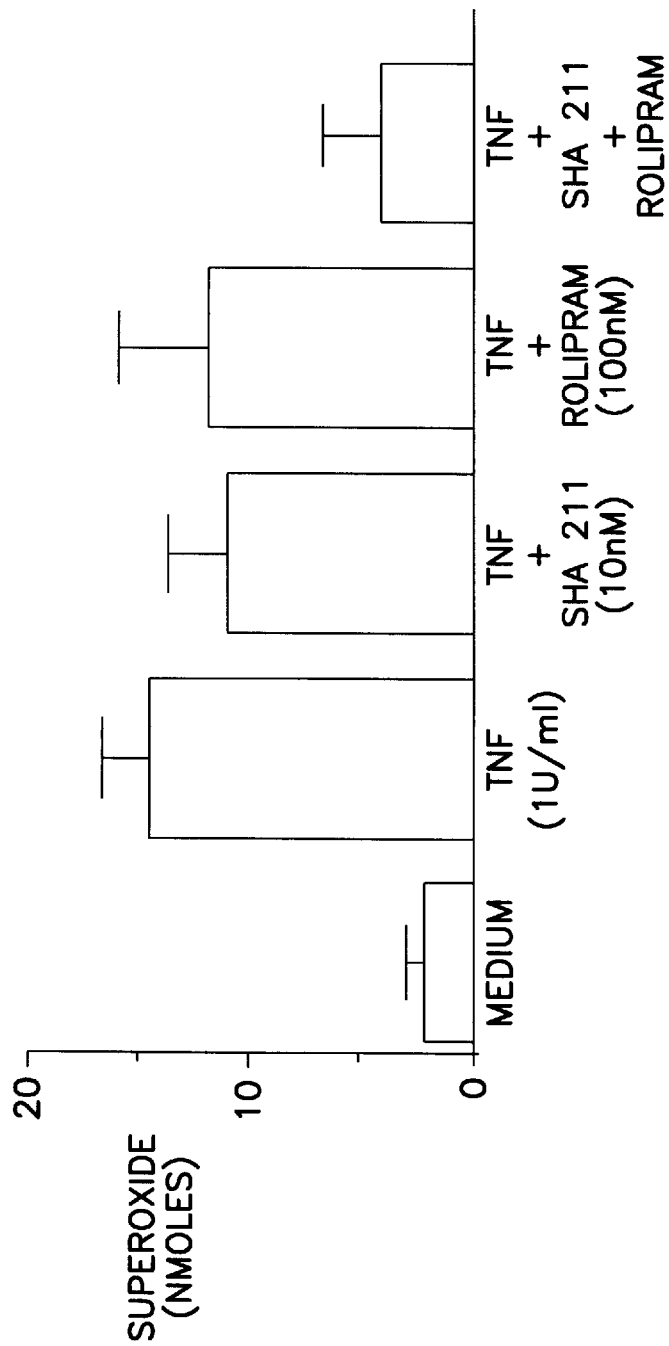

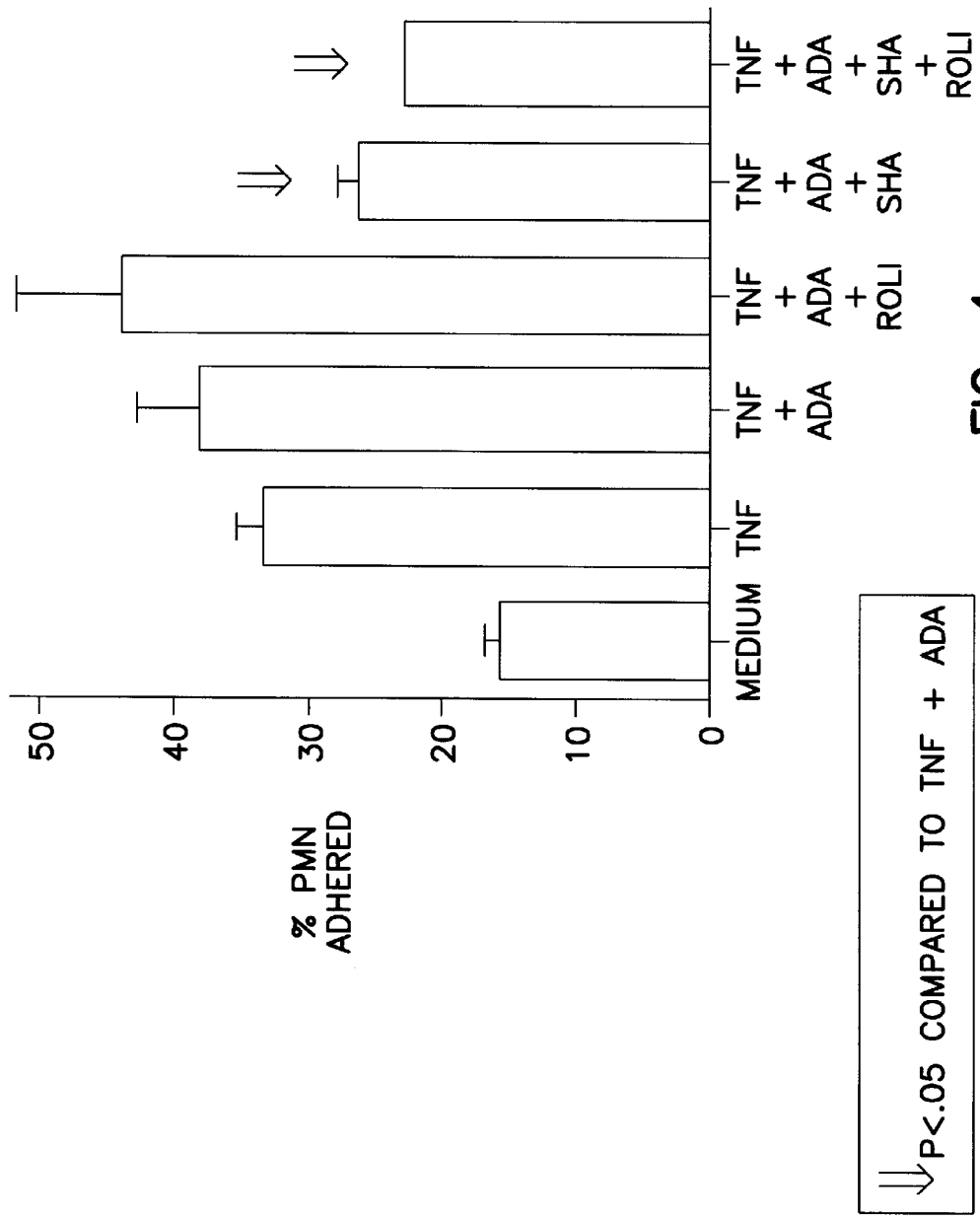

METHOD FOR TREATING INFLAMMATORY DISEASES WITH $A_{2A}$ ADENOSINE RECEPTOR AGONISTS

The present invention was made with the assistance of U.S. Government funding (NIH Grant R01-HL 37942). The U.S. Government may have some rights in this invention.

BACKGROUND OF THE INVENTION

1. Field of the Invention:

The present invention relates to methods and compositions for treating inflammatory diseases.

2. Discussion of the Background:

The release of inflammatory cytokines such as tumor necrosis factor-alpha (TNFα) by leukocytes is a means by which the immune system combats pathogenic invasions, including infections. Cytokines stimulate neutrophils to enhance oxidative (e.g. superoxide and secondary products) and nonoxidative (e.g. myeloperoxidase and other enzymes) inflammatory activity. Inappropriate and over-release of cytokines can produce counterproductive exaggerated pathogenic effects through the release of tissue damaging oxidative and nonoxidative products (Tracey, K. G., et al, *J. Exp. Med.*, vol. 167, pp. 1211–1227 (1988); and Mannel, D. N., et al, *Rev. Infect. Dis.*, vol. 9 (suppl 5), pp. S602–S606 (1987)).

For example, inflammatory cytokines have been shown to be pathogenic in: arthritis (Dinarello, C. A., *Semin. Immunol.*, vol. 4, pp. 133–45 (1992)); ischemia (Seekamp, A., et al, *Agents-Actions-Suppl.*, vol. 41, pp. 137–52 (1993)); septic shock (Mannel, D. N., et al, *Rev. Infect. Dis.*, vol. 9, (suppl 5), pp. S602–S606 (1987)); asthma (Cembrzynska Nowak M., et al, *Am. Rev. Respir. Dis.*, vol. 147, pp. 291–5 (1993)); organ transplant rejection (Imagawa, D. K., et al, *Transplantation*, vol. 51, pp. 57–62 (1991)); multiple sclerosis (Hartung, H.-P., *Ann. Neurol.*, vol. 33, pp. 591–6 (1993)); and AIDS (Matsuyama, T., et al, *AIDS*, vol. 5, pp. 1405–1417 (1991)). In addition, superoxide formation in leukocytes has been implicated in promoting replication of the human immunodeficiency virus (HIV) (Legrand-Poels, S., et al, *AIDS Res. Hum. Retroviruses*, vol. 6, pp. 1389–1397 (1990)).

It is well known that adenosine and some relatively non-specific analogs of adenosine decrease neutrophil production of inflammatory oxidative products (Cronstein, B. N., et al, *Ann. N.Y. Acad. Sci.*, vol. 451, pp. 291–314 (1985); Roberts, P. A., et al, *Biochem. J.*, vol. 227, pp. 669–674 (1985); Schrier, D. J., et al, *J. Immunol.*, vol. 137, pp. 3284–3289 (1986); Cronstein, B. N., et al, *Clinical Immunol. and Immunopath.*, vol. 42, pp. 76–85 (1987); Iannone, M. A., et al, in *Topics and Perspectives in Adenosine Research*, E. Gerlach et al, eds., Springer-Verlag, Berlin, pp. 286–298 (1987); McGarrity, S. T., et al, *J. Leukocyte Biol.*, vol. 44, pp. 411–421 (1988); De La Harpe, J., et al, *J. Immunol.*, vol. 143, pp. 596–602 (1989); McGarrity, S. T., et al, *J. Immunol.*, vol. 142, pp. 1986–1994 (1989); and Nielson, C. P., et al, *Br. J. Pharmacol.*, vol. 97, pp. 882–888 (1989)). For example, adenosine has been shown to inhibit superoxide release from neutrophils stimulated by chemoattractants such as the synthetic mimic of bacterial peptides, f-met-leu-phe (fMLP), and the complement component $C_5a$ (Cronstein, B. N., et al, *J. Immunol.*, vol. 135, pp. 1366–1371 (1985)). Adenosine can decrease the greatly enhanced oxidative burst of PMN first primed with TNFα and then stimulated by a second stimulus such as f-met-leu-phe (Sullivan, G. W., et al, *Clin. Res.*, vol. 41, p. 172A (1993)). There is evidence that in vivo adenosine has anti-inflammatory activity (Firestein, G. S., et al, *Clin. Res.*, vol. 41, p. 170A (1993); and Cronstein, B. N., et al, *Clin. Res.*, vol. 41, p. 244A (1993)).

It has been suggested that there is more than one subtype of adenosine receptor on neutrophils that have opposite effects on superoxide release (Cronstein, B. N., et al, *J. Clin. Invest.*, vol. 85, pp. 1150–1157 (1990)). The existence of $A_{2a}$ receptor on neutrophils was originally demonstrated by Van Calker et al (Van Calker, D., et al, *Eur. J. Pharmacology*, vol. 206, pp. 285–290 (1991)).

There has been progressive development of compounds that are more and more potent and selective as agonists of $A_{2a}$ adenosine receptors based on radioligand binding assays and physiological responses. Initially, compounds with little or no selectivity for $A_{2a}$ receptors were used, such as adenosine itself or 5'-carboxamides of adenosine, such as 5'-N-ethylcarboxamidoadenosine (NECA) (Cronstein, B. N., et al, *J. Immunol.*, vol. 135, pp. 1366–1371 (1985)). Later, it was shown that addition of 2-alkylamino substituents increased potency and selectivity, e.g. CV1808 and CGS21680 (Jarvis, M. F., et al, *J. Pharmacol. Exp. Ther.*, vol. 251, pp. 888–893 (1989)). Additionally, it has been reported that adenosine can decrease the rate of HIV replication in a T-cell line (Sipka, S., et al, *Acta. Biochim. Biopys. Hung.*, vol. 23, pp. 75–82 (1988)). 2-Alkoxy-substituted adenosine derivatives such as WRC0090 are even more potent and selective as agonists on the coronary artery $A_{2a}$ receptor (Ukena, M., et al, *J. Med. Chem.*, vol. 34, pp. 1334–1339 (1991)). The 2-alkylhydrazino adenosine derivatives, e.g. SHA 211 (also called WRC-0470) have also been evaluated as agonists at the coronary artery $A_{2a}$ receptor (Niiya, K., et al, *J. Med. Chem.*, vol. 35, pp. 4557–4561 (1992)).

There is one report of the combination of relatively non-specific adenosine analogs, D-phenylisopropyladenosine (D-PIA) and 2-chloroadenosine (Cl-Ado) with a phosphodiesterase inhibitor resulting in a lowering of neutrophil oxidative activity (Iannone, M. A., et al, in *Topics and Perspectives in Adenosine Research*, E. Gerlach et al, Eds., Springer-Verlag, Berlin, pp. 286–298 (1987)). However, such non-specific analogs are actually more potent activators of $A_1$ adenosine receptors than of $A_{2a}$ adenosine receptors and, thus, are likely to cause side effects due to activation of $A_1$ receptors on other tissues causing effects such as "heart block".

Thus, there remains a need for a method for treating inflammation. There also remains a need for pharmaceutical compositions useful for treating inflammation.

SUMMARY OF THE INVENTION

Accordingly, one object of the present invention is to provide a novel method for treating inflammatory diseases.

It is another object of the present invention to provide novel compositions for the treatment of inflammatory disease.

These and other objects, which will become better understood during the course of the following detailed description, have been achieved by the inventors' discovery that inflammatory diseases may be effectively treated by the administration of drugs which are agonists of $A_{2a}$ adenosine receptors, preferably in combination with a phosphodiesterase inhibitor.

BRIEF DESCRIPTION OF THE DRAWINGS

A more complete appreciation of the invention and many of the attendant advantages thereof will be readily obtained

FIG. 3 illustrates the synergistic effect of SHA 211 and 4-(3-cyclopentyloxy-4-methoxyphenyl)-2-pyrrolidone (ROLIPRAM) in inhibiting TNF-stimulated adherent PMN superoxide release; and FIG. 4 illustrates the effect of SHA 211 with and without 4-(3-cyclopentyloxy-4-methoxyphenyl)-2-pyrrolidone on TNF-stimulated PMN adherence to a fibrinogen coated surface.

DETAILED DESCRIPTION OF THE PREFERRED EMBODIMENTS

Figure 1:
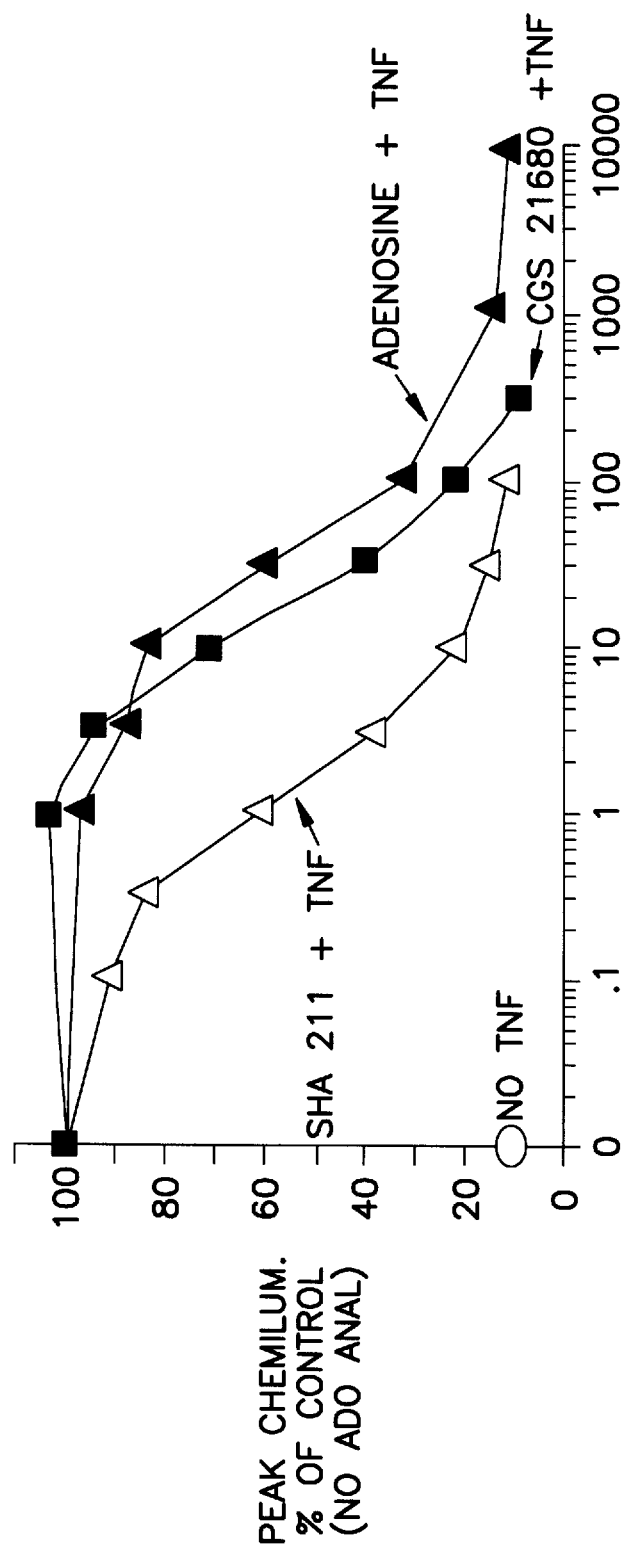
FIG. 1 illustrates the relative potencies of adenosine analogs to modulate TNF-primed fMLP-stimulated PMN chemiluminescence (○, no TNF; Δ, SHA 211+TNF; ■, CGS 21680+TNF; and ▲, adenosine+TNF)

Thus, in a first embodiment, the present invention provides a method for treating inflammatory diseases by administering an effective amount of a compound of formula (I)

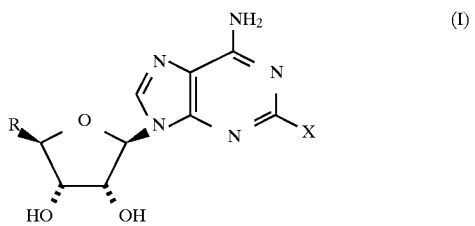

(I)

wherein X is a group selected from the group consisting of $-OR^1$, $-NR^2R^3$, and $-NH-N=R^4$;

wherein $R^1$ is $C_{1-4}$-alkyl; $C_{1-4}$-alkyl substituted with one or more $C_{1-4}$-alkoxy groups, halogens (fluorine, chlorine, or bromine), hydroxy groups, amino groups, mono($C_{1-4}$-alkyl)amino groups, di($C_{1-4}$-alkyl)amino groups, or $C_{6-10}$-aryl groups (wherein the aryl groups may be substituted with one or more halogens (fluorine, chlorine, or bromine), $C_{1-4}$-alkyl groups, hydroxy groups, amino groups, mono($C_{1-4}$-alkyl)amino groups, or di($C_{1-4}$-alkyl)amino groups); $C_{6-10}$-aryl; or $C_{6-10}$-aryl substituted with one or more halogens (fluorine, chlorine, or bromine), hydroxy groups, amino groups, mono($C_{1-4}$-alkyl)amino groups, or di($C_{1-4}$-alkyl)amino groups, or $C_{1-4}$-alkyl groups;

one of $R^2$ and $R^3$ has the same meaning as $R^1$ and the other is hydrogen;

$R^4$ is a group having the formula (II)

(II)

wherein each of $R^5$ and $R^6$ independently may be hydrogen, $C_{3-7}$-cycloalkyl, or any of the meanings of $R^1$, provided that $R^5$ and $R^6$ are not both hydrogen;

R is $-CH_2OH$, $-CO_2H$, $-CO_2R^7$, or $-C(=O)NR^8R^9$; wherein $R^7$ has the same meaning as $R^1$ and wherein $R^8$ and $R^9$ have the same meanings as $R^5$ and $R^6$ and $R^8$ and $R^9$ may both be hydrogen.

Examples of suitable $C_{6-10}$-aryl groups include phenyl and naphthyl.

Such compounds may be synthesized as described in: Hutchinson, A. J., et al, *J. Pharmacol. ExP. Ther.*, vol. 251, pp. 47–55 (1989); Olsson, R. A., et al, *J. Med. Chem.*, vol. 29, pp. 1683–1689 (1986); Bridges, A. J., et al, *J. Med. Chem.*, vol. 31, pp. 1282–1285 (1988); Hutchinson, A. J., et al, *J. Med. Chem.*, vol. 33, pp. 1919–1924 (1990); Ukena, M., et al, *J. Med. Chem.*, vol. 34, pp. 1334–1339 (1991); Francis, J. E., et al, *J. Med. Chem.*, vol. 34, pp. 2570–2579 (1991); Yoneyama, F., et al, *Eur. J. Pharmacol.*, vol. 213, pp. 199–204 (1992); Peet, N. P., et al, *J. Med. Chem.*, vol. 35, pp. 3263–3269 (1992); and Cristalli, G., et al, *J. Med. Chem.*, vol. 35, pp. 2363–2368 (1992); all of which are incorporated herein by reference.

Preferably the compound of formula (I) has X being a group of the formula (III)

(III)

wherein n is an integer from 1–4, preferably 2, and Ar is a phenyl group, tolyl group, xylyl group, or mesityl group. Most preferably Ar is a para-tolyl group and n=2.

Even more preferably, the compound of formula (I) has X being a group of the formula (IV)

(IV)

wherein Cy is a $C_{3-7}$-cycloalkyl group, preferably cyclohexyl.

Specific examples of such compounds of formula (I) include CGS 21680, CV1808, WRC0090, and SHA 211 (WRC0474), shown below:

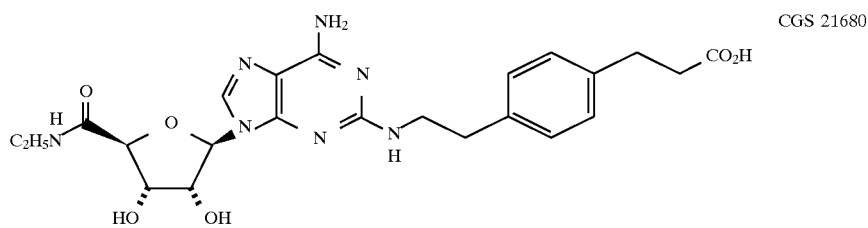

CGS 21680

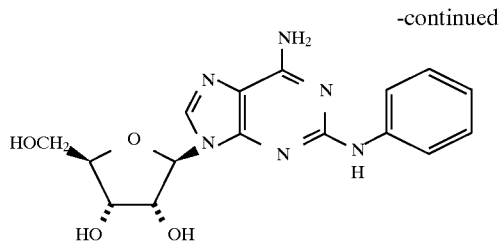

CV1808

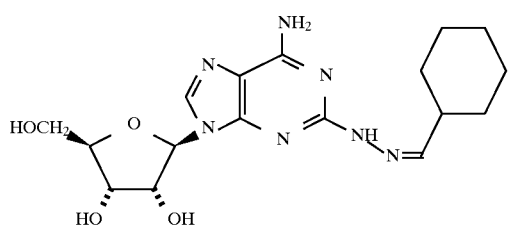

WRC0090

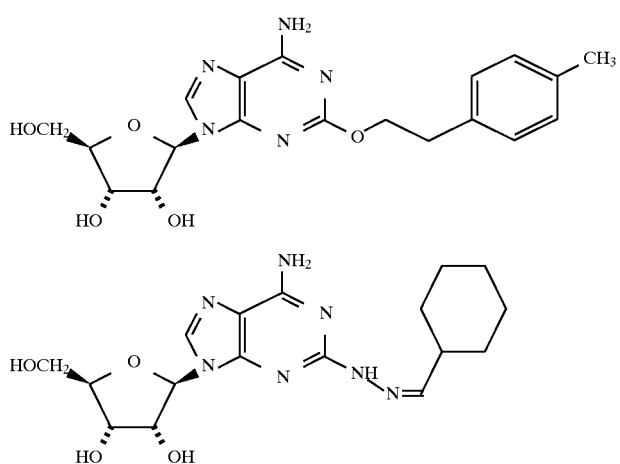

SHA 211
(WRC0474)

Of these specific examples, WRC0090 and SHA 211 (WRC0474) are particularly preferred, and SHA 211 (WRC0474) is very particularly preferred.

Examples of inflammatory diseases which may be treated according to the present invention include:

ischemia, arthritis, asthma, multiple sclerosis, sepsis, septic shock, endotoxic shock, gram negative shock, toxic shock, hemorrhagic shock, adult respiratory distress syndrome, TNF-enhanced HIV replication and TNF inhibition of AZT and DDI activity, organ transplant rejection (including bone marrow, kidney, liver, lung, heart, skin rejection), cachexia secondary to cancer, HIV, and other infections, osteoporosis, infertility from endometriosis, cerebral malaria, bacterial meningitis, adverse effects from amphotericin B treatment, adverse effects from interleukin-2 treatment, adverse effects from OKT3 treatment, and adverse effects from GM-CSF treatment.

The exact dosage of the compound of formula (I) to be administered will, of course, depend on the size and condition of the patient being treated, the exact condition being treated, and the identity of the particular compound of formula (I) being administered. However, a suitable dosage of the compound of formula (I) is 0.5 to 100 μg/kg of body weight, preferably 1 to 10 μg/kg of body weight. Typically, the compound of formula (I) will be administered from 1 to 8, preferably 1 to 4, times per day.

The preferred mode of administration of the compound of formula (I) may also depend on the exact condition being treated. However, most typically, the mode of administration will be intravenous, parenteral, subcutaneous, or intramuscular injection.

Of course, it is to be understood that the compound of formula (I) may be administered in the form of a pharmaceutically acceptable salt. Examples of such salts include acid addition salts. Preferred pharmaceutically acceptable addition salts include salts of mineral acids, for example, hydrochloric acid, sulfuric acid, nitric acid, and the like; salts of monobasic carboxylic acids, such as, for example, acetic acid, propionic acid, and the like; salts of dibasic carboxylic acids, such as maleic acid, fumaric acid, oxalic acid, and the like; and salts of tribasic carboxylic acids, such as, carboxysuccinic acid, citric acid, and the like. In the compounds of formula (I) in which R is —$CO_2H$, the salt may be derived by replacing the acidic proton of the —$CO_2H$ group with a cation such as $Na^+$, $K^+$, $NH_4^+$, mon-, di, tri, or tetra($C_{1-4}$-alkyl)ammonium, or mono-, di-, tri-, or tetra($C_{2-4}$-alkanol)ammonium.

It is also to be understood that many of the compounds of formula (I) may exist as various isomers, enantiomers, and diastereomers and that the present invention encompasses the administration of a single isomer, enantiomer, or diastereomer in addition to the administration of mixtures of isomers, enantiomers, or diastereomers.

The compounds of formula (I) can be administered orally, for example, with an inert diluent with an edible carrier. They can be enclosed in gelatin capsules or compressed into tablets. For the purpose of oral therapeutic administration, the compounds can be incorporated with excipients and used in the form of tablets, troches, capsules, elixirs, suspensions, syrups, waters, chewing gums, and the like. These preparations should contain at least 0.5% by weight of the compound of formula (I), but the amount can be varied depending upon the particular form and can conveniently be between 4.0% to about 70% by weight of the unit dosage. The amount of the compound of formula (I) in such compositions is such that a suitable dosage will be obtained. Preferred compositions and preparations according to the present invention are prepared so that an oral dosage unit form contains between about 30 μg and about 5 mg, preferably between 50 to 500 μg, of active compound.

Tablets, pills, capsules, troches, and the like can contain the following ingredients: a binder, such as micro-crystalline cellulose, gum tragacanth or gelatin; an excipient, such as starch or lactose; a disintegrating agent, such as alginic acid, Primogel, corn starch, and the like; a lubricant, such as magnesium stearate or Sterotes; a glidant, such as colloidal silicon dioxide; a sweetening agent, such as sucrose, saccharin or aspartame; or flavoring agent, such as peppermint, methyl salicylate, or orange flavoring. When the dosage unit form is a capsule it can contain, in addition to the compound of formula (I), a liquid carrier, such as a fatty oil.

Other dosage unit forms can contain other materials that modify the physical form of the dosage unit, for example, as coatings. Thus, tablets or pills can be coated with sugar, shellac, or other enteric coating agents. A syrup may contain, in addition to the active compounds, sucrose as a sweetening agent and preservatives, dyes, colorings, and flavors. Materials used in preparing these compositions should be pharmaceutically pure and non-toxic in the amounts used.

For purposes of parenteral therapeutic administration, the compounds of formula (I) can be incorporated into a solution or suspension. These preparations should contain at least 0.1% of the aforesaid compound, but may be varied between 0.5% and about 50% of the weight thereof. The amount of active compound in such compositions is such that a suitable dosage will be obtained. Preferred compositions and preparations according to the present invention are prepared so that a parenteral dosage unit contains between 30 µg to 5 mg, preferably between 50 to 500 µg, of the compound of formula (I).

Solutions or suspensions of the compounds of formula (I) can also include the following components: a sterile diluent, such as water for injection, saline solution, fixed oils, polyethylene glycols, glycerine, propylene glycol or other synthetic solvents: antibacterial agents, such as benzyl alcohol or methyl parabens; antioxidants, such as ascorbic acid or sodium bisulfite; chelating agents, such as ethylenediaminetetraacetic acid; buffers, such as acetates, citrates or phosphates; and agents for the adjustment of tonicity, such as sodium chloride or dextrose. The parenteral preparation can be enclosed in ampoules, disposable syringes or multiple dose vials made of glass or plastic.

In a particularly preferred embodiment, the present method involves the administration of a Type IV phosphodiesterase inhibitor in addition to the compound of formula (I). Examples of Type IV phosphodiesterase inhibitors include those disclosed in U.S. Pat. Nos. 3,892,777, 4,665,074, 4,965,271, 5,096,906, 5,124,455, 5,272,153, and 4,193,926, and WO 92-079778, and Molnar-Kimber, K. L., et al, *J. Immunol.*, vol. 150, p. 295A (1993), all of which are incorporated herein by reference.

Specifically, the suitable Type IV phosphodiesterase inhibitors include compounds of the formulae (II), (III), (IV), (V), (VI) and (VII):

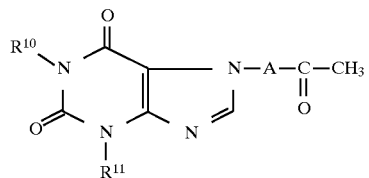
(II)

(disclosed and described in U.S. Pat. No. 5,272,153) in which $R^{10}$ and $R^{11}$ are the same or different and are independently selected from the group consisting of straight-chain or branched-chain alkyl radicals with 2 to 6 carbon atoms, cyclohexyl, straight chain or branched chain alkoxyalkyl, and hydroxyalkyl radicals; and A is a hydrocarbon radical with up to 4 carbon atoms which can be substituted by a methyl group.

A more detailed description of the compounds of formula (II) employed in this invention and methods of preparing the compounds are contained in U.S. Pat. No. 4,242,345, the entire disclosure of which is relied upon and incorporated by reference herein.

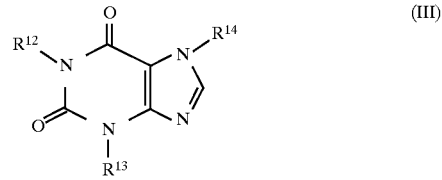
(III)

(disclosed and described in U.S. Pat. Nos. 5,096,906 and 5,272,153) wherein: (a) at least one of $R^{12}$ and $R^{14}$ is either a branched hydroxyalkyl group of the formula

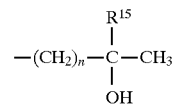

with a tertiary alcohol function, in which $R^{15}$ stands for an alkyl group with 1 to 3 carbon atoms and n stands for a whole number from 2 to 5, the other $R^{12}$ or $R^{14}$ group that may optionally be present stands for a hydrogen atom or an aliphatic hydrocarbon group $R^{16}$ with up to 6 carbon atoms, whose carbon chain may be interrupted by up to 2 oxygen atoms or may be substituted with a hydroxy or oxo group; and $R^{13}$ represents an alkyl group with 1 to 4 carbon atoms; or (b) at least one of $R^{12}$ or $R^{14}$ is an oxoallyl group of the formula

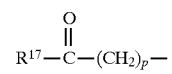

wherein $R^{17}$ is $C_1$-$C_6$ alkyl, and p=2, 3, or 4, the other $R^{12}$ or $R^{14}$ being defined as above; and $R^{13}$ represents an alkyl group with 1 to 4 carbon atoms; or (C) $R^{12}$, $R^{13}$, and $R^{14}$ are the same or different and are selected from the group consisting of (i) $C_1$-$C_6$ straight or branched chain alkyl; (ii) $C_1$-$C_6$ straight or branched chain alkoxyalkyl; (iii) $C_1$-$C_6$ straight or $C_{1-9}$ branched chain hydroxyalkyl; and in addition $R^{12}$ and $R^{13}$ can be cyclohexyl.

Among the compounds of formula (III) are pentoxifylline (Trental®) and lysophylline [1-(5R-hydroxylhexyl)-3,7-dimethylxanthine]. Other compounds can be prepared according to the disclosure of U.S. Pat. No. 3,737,433 and Belgium Patent 831,051 (where $R^{12}/R^{14}$ are oxoallyl). For the cases where at least one of $R^{12}/R^{14}$ is a tertiary alcohol reference may be had to the international application PCT-EP-86-00401, Jul. 8, 1986.

Racemic and optically active 4-(polyalkoxyphenyl)-2-pyrrolidones of general formula (IV)

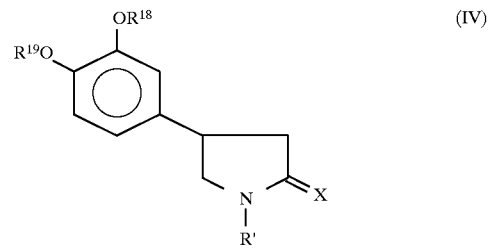
(IV)

(disclosed and described in U.S. Pat. No. 4,193,926) wherein $R^{18}$ and $R^{19}$ each are alike or different and are hydrocarbon radicals having up to 18 carbon atoms with at least one being other than methyl, a heterocyclic ring, or alkyl of 1–5 carbon atoms which is substituted by one or more of halogen atoms, hydroxy, carboxy, alkoxy, alkoxycarbonyl or an amino group; amino; R' is a hydrogen atom, alkyl, aryl or acyl; and X is an oxygen atom or a sulfur atom.

Examples of hydrocarbon $R^{18}$ and $R^{19}$ groups are saturated and unsaturated, straight-chain and branched alkyl of 1–18, preferably 1–5, carbon atoms, cycloalkyl and cycloalkylalkyl, preferably of 3–7 carbon atoms, and aryl and aralkyl, preferably of 6–10 carbon atoms, especially monocyclic.

Examples of alkyl are methyl, ethyl, propyl, isopropyl, butyl, isobutyl, tert-butyl, pentyl, 2-methylbutyl, 2,2-dimethylpropyl, hexyl, heptyl, octyl, nonyl, 1,2-dimethylheptyl, decyl, undecyl, dodecyl and stearyl, with the proviso that when one of $R^{18}$ and $R^{19}$ is methyl, the other is a value other than methyl. Examples of unsaturated alkyl groups are alkenyl and alkynyl, e.g., vinyl, 1-propenyl, 2-propenyl, 2-propynyl and 3-methyl-2-propenyl.

Examples of cycloalkyl and cycloalkylalkyl which preferably contain a total of 3–7 carbon atoms are cyclopropyl, cyclopropylmethyl, cyclopentyl and cyclohexyl.

Examples of aryl and aralkyl are phenyl and benzyl, which are preferred, and tolyl, xylyl, naphthyl, phenethyl and 3-phenylpropyl.

Examples of heterocyclic $R^{18}$ and $R^{19}$ groups are those wherein the heterocyclic ring is saturated with 5 or 6 ring members and has a single O, S or N atom as the hetero atom, e.g., 2- and 3-tetrahydrofuryl, 2- and 3-tetrahydropyranyl, 2- and 3-tetrahydrothiophenyl, pyrrolidino, 2- and 3-pyrrolidyl, piperidino, 2-, 3- and 4-piperidyl, and the corresponding N-alkyl-pyrrolidyl and piperidyl wherein alkyl is of 1–4 carbon atoms. Equivalents are heterocyclic rings having fewer or more, e.g., 4 and 7, ring members, and one or more additional hetero atoms as ring members, e.g., morpholino, piperazino and N-alkylpiperazino.

Examples of substituted alkyl $R^{18}$ and $R^{19}$ groups, preferably of 1–5 carbon atoms, are those mono- or polysubstituted, for example, by halogen, especially fluorine, chlorine and bromine. Specific examples of such halogen-substituted alkyl are 2-chloroethyl, 3-chloropropyl, 4-bromobutyl, difluoromethyl, trifluoromethyl, 1,1,2-trifluoro-2-chloroethyl, 3,3,3-trifluoropropyl, 2,2,3,3,3-pentafluoropropyl and 1,1,1,3,3,3-hexafluoro-2-propyl. Examples of other suitable substituents for such alkyl groups are hydroxy groups, e.g., 2-hydroxyethyl or 3-hydroxypropyl; carboxy groups, e.g., carboxymethyl or carboxyethyl; alkoxy groups, wherein each alkoxy group contains 1–5 carbon atoms, e.g., ethoxymethyl, isopropoxymethyl, 2-methoxyethyl, 2-isopropoxyethyl, 2-butyoxyethyl, 2-isobutyoxyethyl, and 3-pentoxypropyl.

Also suitable as preferably terminal-positioned substituents on alkyl groups of 1–5 carbon atoms are alkoxycarbonyl of 1–5 carbon atoms in the alkoxy group. Examples of such alkoxycarbonyl substituted alkyl groups are ethoxycarbonylmethyl and 2-butoxycarbonylethyl.

Alkyl groups of 1–5 carbon atoms can also be substituted, e.g., in the β, γ and preferably terminal position with amino groups wherein the nitrogen atom optionally is mono- or disubstituted by alkyl, preferably of 1–5 carbon atoms, or is part of a 4- to 7-membered ring.

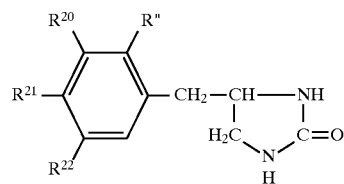

(disclosed and described in U.S. Pat. No. 3,892,777) in which R" is halogen, hydrogen, $C_{1-4}$-alkyl or $C_{1-4}$ alkoxy and $R^{20}$, $R^{21}$, and $R^{22}$ taken independently of each other are hydrogen, hydroxy, $C_{1-4}$ alkoxy and hydroxy-$C_{1-4}$ alkoxy and R", $R^{20}$, $R^{21}$, or $R^{22}$ taken as an adjacent pair is alkylenedioxy.

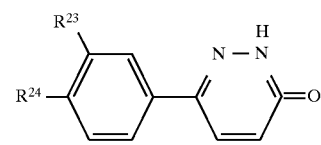

(disclosed and described in U.S. Pat. No. 4,665,074) in which one of the substituents $R^{23}$ and $R^{24}$ denotes hydrogen or C1-C4-alkoxy, and the other denotes polyfluoro-C1-C4-alkoxy, and their pharmacologically-tolerated salts with bases. In this context, polyfluoro-C1-C4-alkoxy is straight-chain or branched C1-C4-alkoxy in which at least two hydrogen atoms are replaced by fluorine atoms. A straight-chain C1-C3-alkoxy group in which at least two hydrogen atoms are replaced by fluorine is preferred. Preferred polyfluoroalkoxy groups are difluoromethoxy, trifluoromethoxy, 1,1,2,2-tetrafluoroethoxy and 1,1,1-trifluoroethoxy. C1-C4-alkoxy is straight-chain or branched. The methoxy group is preferred.

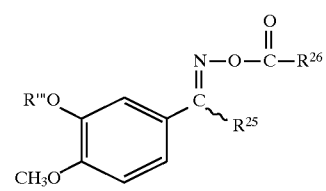

(disclosed and described in U.S. Pat. No. 5,124,455) wherein R''' is $C_{3-7}$-alkyl, $C_{3-7}$-cycloalkyl,

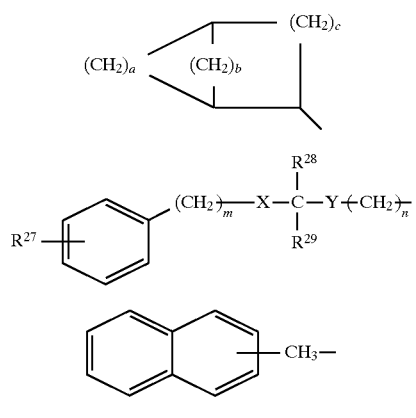

OR

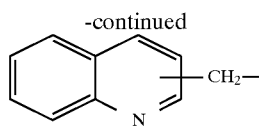

$R^{25}$ is hydrogen, lower alkyl or

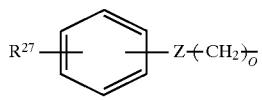

a is 1–3;
b is 1–3;
c is 0–2;
X, Y, and Z are each, independently, a bond, O, S, or NH, with the proviso that if one of X or Y is O, S, or NH, the other must be a bond;
$R^{26}$ is amino loweralkylamino, arylamino, loweralkoxy, or aryloxy;
$R^{27}$ is hydrogen, halo, hydroxy, loweralkoxy, aryloxy, loweralkanoyloxy, amino, loweralkylamino, arylamino or loweralkanoylamino;
$R^{28}$ and $R^{29}$ are each, independently hydrogen or lower alkyl;
m is 0–4;
n is 1–4; and
o is 1–4.

The terms "lower alkyl", "lower alkoxy" and "lower alkanoyl" refer to moieties having 1 to 6 carbon atoms in the carbon chain. The term "aryl" refers to aromatic moieties having 6–10 carbon atoms (including phenyl and naphthyl). The term "halo" refers to fluoro, chloro and bromo.

Specific examples of preferred Type IV phosphodiesterase inhibitors include 1,3-dibutyl-7-[2'-oxopropyl]-xanthine, 1-(5'-oxohexyl)-3,7-dimethylxanthine, 4-(3-cyclopentyloxy-4-methoxyphenyl)-2-pyrrolidone, 4-(3-butoxy-4-methoxybenzyl)-2-imidazolidinone, 1-(3-(cyclopentyloxy)-4-methoxyphenyl)ethanone[E]-O-(aminocarbonyl)oxime, 6-(4-difluoromethoxy-3-methoxyphenyl)-3(2H)pyridazinone, and 1-(5R-hydroxyhexyl)-3,7-dimethylxanthine.

Effective amounts of the Type IV phosphodiesterase inhibitor can be administered to a subject by any one of various methods, for example, orally as in a capsule or tablets, or parenterally in the form of sterile solutions. The Type IV phosphodiesterase inhibitors, while effective themselves, can be formulated and administered in the form of their pharmaceutically acceptable addition salts for purposes of stability, convenience of crystallization, increased solubility, and the like.

Preferred pharmaceutically acceptable addition salts include salts of mineral acids, for example, hydrochloric acid, sulfuric acid, nitric acid, and the like; salts of monobasic carboxylic acids, such as, for example, acetic acid, propionic acid, and the like; salts of dibasic carboxylic acids, such as maleic acid, fumaric acid, oxalic acid, and the like; and salts of tribasic carboxylic acids, such as, carboxysuccinic acid, citric acid, and the like.

The Type IV phosphodiesterase may be administered in the form of a pharmaceutical composition similar to those described above in the context of the compound of formula (I).

While dosage values will vary with the specific disease condition to be alleviated, good results are achieved when the Type IV phosphodiesterase inhibitors of formula (II), (III), (IV), (V), (VI), or (VII) are administered to a subject requiring such treatment as an effective oral, parenteral or intravenous dose as described below.

Thus, for the type IV phosphodiesterase inhibitors of formulae (II) and (III), while dosage values will vary with the specific disease condition to be alleviated, good results are achieved when the xanthines of formula (II) or formula (III) are administered to a subject requiring such treatment as an effective oral, parenteral or intravenous dose of from 0.01 to 25 mg/kg of body weight per day. A particularly preferred effective amount is about 0.1 to 1.0 mg/kg of body weight per day. In general, daily dosages will vary from 1–1,000 mg, preferably 10–600 mg per day.

In the case of the phosphodiesterase inhibitors of formulae (IV) and (VII), for oral administration, the amount of active agent per oral dosage unit usually is 0.1–20 mg, preferably 0.5–10 mg. The daily dosage is usually 0.1–50 mg, preferably 1–30 mg. p.o. For parenteral application, the amount of active agent per dosage unit is usually 0.005–10 mg, preferably 0.01–5 mg. The daily dosage is usually 0.01–20 mg, preferably 0.02–5 mg i.v. or i.m.

For the compounds of formula (V), it is preferable to provide a daily dose in the range of from about 2.5 mg to about 600 mg, generally in divided doses.

In the case of the phosphodiesterase inhibitors of formula (VI), when in the form of unit doses, the pharmaceutical formulations contain, e.g., from about 0.5 to 250 mg, advantageously from 1 to 200 mg and in particular from 2 to 100 mg, of active compound. Parenteral formulations contain, e.g., from about 0.1 to 50 mg, advantageously from 0.3 to 10 mg and in particular from 0.5 to 25 mg, of active compound. The active compound or compounds are generally administered in a daily dose of from 0.01 to 10, preferably from 0.03 to 5 and in particular from 0.05 to 3, mg/kg of body weight, if appropriate in the form of several, preferably 0.1 to 3, individual administrations to achieve the desired results. An individual administration contains the active compound or compounds in amounts of from 0.01 to 5, preferably from 0.02 to 3 and in particular from 0.04 to 2, mg/kg of body weight. For administration by inhalation, it is advantageous to administer the active compound or compounds in a daily dose of from 0.01 to 10 mg, preferably from 0.05 to 5 mg and in particular from 0.1 to 3 mg, if appropriate in the form of several, preferably 0.1 to 3, individual doses.

It is to be understood, however, that for any particular subject, specific dosage regimens should be adjusted to the individual need and the professional judgement of the person administering or supervising the administration of the Type IV phosphodiesterase inhibitor. It is to be further understood that the dosages set forth herein are exemplary only and that they do not, to any extent, limit the scope or practice of the present invention.

In a particularly preferred embodiment, the compound of formula (I) and the Type IV phosphodiesterase inhibitor are coadministered together in a single dosage unit. The compound of formula (I) and the type IV phosphodiesterase inhibitor may be administered in the same type of pharmaceutical composition as those described above in the context of the compound of formula (I).

By coadministering a type IV phosphodiesterase inhibitor with the agonist of the $A_{2a}$ adenosine receptor it is possible to dramatically lower the dosage of the $A_{2a}$ adenosine receptor agonist and the Type IV phosphodiesterase inhibitor due to a synergistic effect of the two agents. Thus, in the embodiment involving coadministration of the $A_{2a}$ adenosine receptor agonist with the type IV phosphodiesterase inhibitor, the dosage of the $A_{2a}$ adenosine receptor agonist may be reduced by a factor of 5 to 10 from the dosage used when no type IV phosphodiesterase inhibitor is administered. This reduces the possibility of side effects.

The present invention will now be described in more detail in the context of the administration of CGS21680, CV1808, WRC0090, and SHA 211 and the coadministration of SHA 211 and 4-(3-cyclopentyloxy-4-methoxyphenyl)-2-pyrrolidone. However, it is to be understood that the present invention may be practiced with other compounds of formula (I) and other Type IV phosphodiesterase inhibitors.

It has been established that CGS21680 and CV1808 have in vitro anti-inflammatory activity in neutrophils. These data suggest that adenosine $A_{2a}$ receptors mediate these responses. The present data given below indicate that the potency order of adenosine analogs as inhibitors of inflammatory activity in neutrophils is SHA 211>CGS21680>adenosine (FIG. 1). This demonstrates that the response is mediated by $A_{2a}$ receptors. Based on radioligand binding data the selectivity and potency of these compounds is SHA 211>WRC0090>CGS21680= CV1808>NECA>=adenosine. The advantage of more potent and selective compounds such as SHA 211 and WRC0090 over adenosine and previously reported adenosine analogs such as CGS21680 and CV1808 is that the administration of SHA 211 or WRCOO90 reduces the possibility of side effects mediated by the binding of the analogs to other adenosine receptors, e.g. minimizing heart block mediated by $A_1$ adenosine receptors.

Other features of the invention will become apparent in the course of the following descriptions of exemplary embodiments which are given for illustration of the invention and are not intended to be limiting thereof.

EXAMPLES
MATERIALS AND METHODS

Materials: f-Met-Leu-Phe(fMLP), luminol, and trypan blue were from Sigma Chemical. Ficoll-hypaque was purchased from Flow Laboratories (McLean, Va.) and Los Alamos Diagnostics (Los Alamos, N. Mex.). Hanks balanced salt solution (HBSS), and limulus amebocyte lysate assay kit were from Whittaker Bioproducts (Walkersville, Md.). Human serum albumin (HSA) was from Cutter Biological (Elkhart, Ind.). Recombinant human tumor necrosis factor-alpha was supplied by Dianippon Pharmaceutical Co. Ltd. (Osaka, Japan).

Leukocyte Preparation: Purified PMN (~98% PMN and >95% viable by trypan blue exclusion) containing <1 platelet per 5 PMN and <50 pg/ml endotoxin (limulus amebocyte lysate assay) were obtained from normal heparinized (10 Units/ml) venous blood by a one step ficoll-hypaque separation procedure (Ferrante, A., et al, J. Immunol. Meth., vol. 36, p. 109, (1980)). Residual RBC were lysed by hypotonic lysis with iced 3 ml 0.22% sodium chloride solution for 45 seconds followed by 0.88 ml of 3% sodium chloride solution.

Chemiluminescence: Luminol enhanced chemiluminescence, a measure of neutrophil oxidative activity, is dependent upon both superoxide production and mobilization of the granule enzyme myeloperoxidase. The light is emitted from unstable high-energy oxygen species generated by activated neutrophils. Purified PMN ($5\times10^5$/ml) were incubated in HBSS containing 0.1% human serum albumin (1 ml) with or without adenosine, adenosine analogs, and TNFA (1 U/mL) for 30 minutes at 37° C. in a shaking water bath. Then luminol ($1\times10^{-4}$M) enhanced f-met-leu-phe (1 $\mu$M) stimulated chemiluminescence was read with a Chronolog Photometer (Chrono-log Corp., Havertown, PA) at 37° C. for 8 min. Chemiluminescence is reported as relative peak light emitted (=height of the curve) compared to samples with TNF and without adenosine or adenosine analogs. SHA 211 was 10 times more potent than either adenosine (ADO) or CGS21680 in decrease TNF-primed f-met-leu-phe-stimulated PMN chemiluminescence (see FIG. 1).

Synergy of $A_{2a}$ Adenosine Receptor Agonist and Phosphodiesterase Inhibitors.

The synergy between SHA 211 and 4-(3-cyclopentyloxy-4-methoxyphenyl)-2-pyrrolidone (a potent inhibitor of leukocyte type IV phosphodiesterases) was examined by measuring the effect of combined 4-(3-cyclopentyloxy-4-methoxyphenyl)-2-pyrrolidone and SHA 211 on TNF-primed f-met-leu-phe-stimulated suspended neutrophil superoxide release and on the oxidative burst of neutrophils adhering to matrix proteins (in this model the PMN oxidative burst is enhanced by small concentrations of TNF [e.g. 1 U/ml] without the addition of a second stimulus such as the peptide f-met-leu-phe).

Suspended PMN Superoxide Release: Human PMN ($1\times10^6$/ml) from Ficoll-Hypaque separation were primed for 30 minutes (37° C.) with or without rhTNF (10 U/ml), with adenosine deaminase (1 U/ml), and with or without 4-(3-cyclopentyloxy-4-methoxyphenyl)-2-pyrrolidone and SHA 211. Cytochrome c (120 $\mu$M), catalase (0.062 mg/ml) and fMLP (100 nM) were added and the samples incubated for 10 minutes more at 37° C. SOD (200 U/ml) was added to matched samples. The samples were iced and centrifuged (2000 g×10 minutes). The optical density of the supernatants were read at 550 nm against the matched SOD samples, and the nmoles of SOD-inhibitable superoxide released in 10 minutes were calculated.

Figure 2:
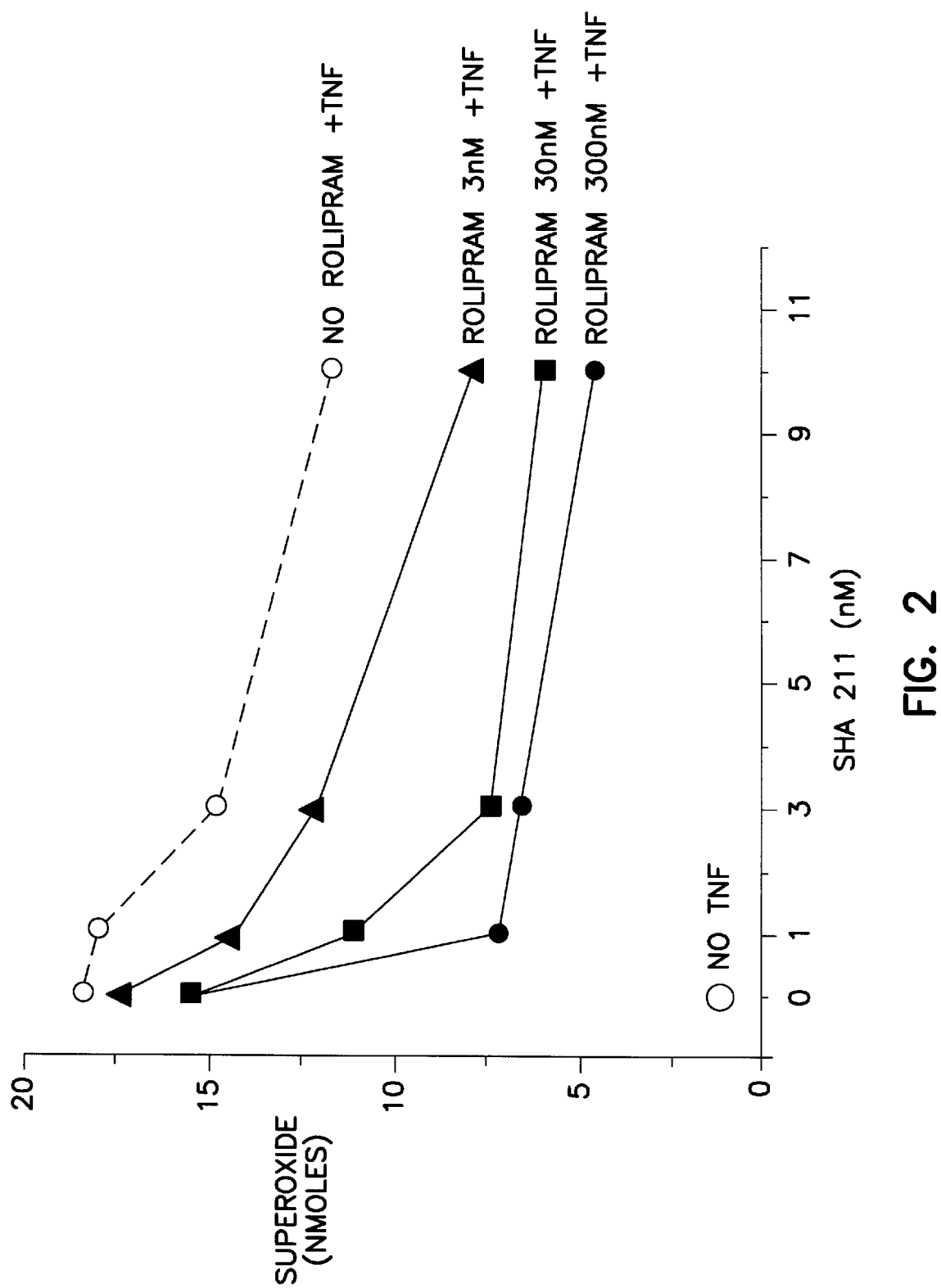
FIG. 2 illustrates the synergistic effect of SHA 211 and 4-(3-cyclopentyloxy-4-methoxyphenyl)-2-pyrrolidone (ROLIPRAM) in inhibiting TNF-primed (10 U/ml), fMLP-stimulated (100 nM) PMN superoxide production (○, no 4-(3-cyclopentyloxy-4-methoxyphenyl)-2-pyrrolidone; ▲, 3 nM 4-(3-cyclopentyloxy-4-methoxyphenyl)-2-pyrrolidone; ■, 30 nM 4-(3-cyclopentyloxy-4-methoxyphenyl)-2-pyrrolidone; ●, 300 nM 4-(3-cyclopentyloxy-4-methoxyphenyl)-2-pyrrolidone)

A synergistic effect of SHA 211 and 4-(3-cyclopentyloxy-4-methoxyphenyl)-2-pyrrolidone in decreasing the TNF-primed fMLP-stimulated PMN oxidative burst was observed (see FIG. 2).

TNF-stimulated superoxide release of PMN adherent to a matrix protein (fibrinogen) coated surface: Human PMN ($1\times10^6$/ml) from Ficoll-Hypaque separation were incubated for 90 minutes in 1 ml of Hanks balanced salt solution containing 0.1% human serum albumin, cytochrome c (120 $\mu$M), and catalase (0.062 mg/ml) in the presence and absence of rhTNF (1 U/ml), SHA 211 (10 nM) and 4-(3-cyclopentyloxy-4-methoxyphenyl)-2-pyrrolidone (100 nM) in a tissue culture well which had been coated overnight with human fibrinogen. SOD (200 U/ml) was added to matched samples. The supernatants were iced and centrifuged (2000 g×10 minutes) to remove any remaining suspended cells, and the optical density of the supernatants were read at 550 mn against the matched SOD samples, and the nmoles of SOD-inhibitable superoxide released in 90 minutes were calculated.

A synergistic effect of SHA 211 and 4-(3-cyclopentyloxy-4-methoxyphenyl)-2-pyrrolidone in decreasing the TNF-stimulated release of superoxide from PMN adherent to fibrinogen was observed (see FIG. 3).

Effect of SHA 211 with and without 4-(3-Cyclopentyloxy-4-methoxyphenyl)-2-pyrrolidone on TNF-Stimulated PMN Adherence to a Fibrinogen-Coated Surface.

Cronstein et al, J. Immunol., vol. 148, p. 2201 (1992) reported that adenosine binding to A1 receptors increases PMN adherence to endothelium and matrix proteins and binding to A2 receptors decreases adherence to these surfaces when the PMN are stimulated with fMLP. Despite this, others have failed to see much of an effect of adenosine (10 $\mu$M) on TNF-stimulated PMN adherence to matrix proteins.

In contrast, adenosine dramatically decreases the oxidative burst of TNF-stimulated PMN adhering to matrix proteins (DeLa Harpe, J., *J. Immunol.* vol. 143, p. 596 (1989)).

PMN adherence to fibrinogen was measured as follows as adapted from Hanlon, *J. Leukocyte Biol.,* vol. 50, p. 43 (1991). Twenty-four well flat-bottomed tissue culture plates were incubated (37° C.) overnight with 0.5 ml of fibrinogen (5 mg/ml) dissolved in 1.5% $NaHCO_3$. The plates were emptied and each well washed 2× with 1 ml of normal saline. The wells were then filled with 1 ml of HBSS-0.1% human serum albumin containing PMN ($1 \times 10^6$/ml) with and without rhTNFα(1 U/ml), ADA 1 U/ML, SHA 211 (10 nM), CGS21680 (30 nM), adenosine (100 nM) and 4-(3-cyclopentyloxy-4-methoxyphenyl)-2-pyrrolidone (ROLIPRAM) (100 nM). The plates were incubated for 90 minutes at 37° C. in 5% $CO_2$. Following incubation the tissue culture wells were washed free of non-adherent cells with normal saline. The adherent monolayer of PMN was lysed with 0.1% triton-X, the amount of lactic dehydrogenase (LDH) released from the monolayer assayed (LDH kit, Sigma Co., St. Louis, Mo.), and compared to a standard curve relating the LDH content to PMN numbers. The results are shown in FIG. 4.

The experiments described above establish that SHA 211 decreases TNF-stimulated oxidative activity of PMN adhering to fibrinogen, especially when combined with ROLIPRAM. These data indicate that SHA 211 (10 nM) decreases TNF-stimulated PMN adherence to fibrinogen. As a comparison to SHA 211 (at only 10 nM), CGS21680 (30 nM) decreased TNF-stimulated adherence in the presence of ADA from 38% to 30% adhered (p=.004), and ten times as much adenosine (100 nM) decreased adherence to 28% adhered (p=0.009 compared to TNF in the presence of ADA).

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A method of treating inflammatory diseases other than ischemia, comprising administering to a patient in need thereof an effective amount of an agonist of an A2A adenosine receptor of formula (I)

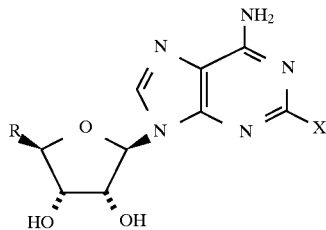

wherein X is a group selected from the group consisting of —$OR^1$, —$NR^2R^3$, and —NH—N=$R^4$;

wherein $R^1$ is $C_{1-4}$-alkyl; $C_{1-4}$-alkyl substituted with one or more $C_{1-4}$-alkoxy groups, halogens (fluorine, chlorine, or bromine), hydroxy groups, amino groups, mono ($C_{1-4}$-alkyl) amino groups, di($C_{1-4}$-alkyl) amino groups, or $C_{6-10}$-aryl groups (wherein the aryl groups may be substituted with one or more halogens (fluorine, chlorine, or bromine), $C_{1-4}$-alkyl groups, hydroxy groups, amino groups, mono ($C_{1-4}$-alkyl) amino groups, or di($C_{1-4}$-alkyl) amino groups); $C_{6-10}$-aryl; or $C_{6-10}$-aryl substituted with one or more halogens (fluorine, chlorine, or bromine), hydroxy groups, amino groups, mono ($C_{1-4}$-alkyl) amino groups, or di($C_{1-4}$-alkyl) amino groups, or $C_{1-4}$-alkyl groups;

One of $R^2$ and $R^3$ has the same meaning as $R^1$ and the other is hydrogen;

$R^4$ is a group having the formula

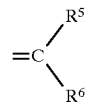

wherein each of $R^5$ and $R^6$ independently may be hydrogen, $C_{3-7}$-cycloalkyl, or any of the meanings of $R^1$, provided that $R^5$ and $R^6$ are not both hydrogen;

R is —$CH_2OH$, —$CO_2H$, —$CO^2R^7$, or —C(=O)$NR^8R^9$; wherein $R^7$ has the same meaning as $R^1$ and wherein $R^8$ and $R^9$ have the same meanings as $R^5$ and $R^6$, and $R^8$ and $R^9$ can both be hydrogen; or a pharmaceutically acceptable salt thereof.

2. The method of claim 1, wherein said disease is selected from the group consisting of: arthritis, asthma, multiple sclerosis, sepsis, septic shock, endotoxic shock, gram negative shock, toxic shock, hemorrhagic shock, adult respiratory distress syndrome, TNF-enhanced HIV replication, TNF inhibition of AZT and DDI activity, organ transplant rejection, cachexia secondary to cancer, HIV, osteoporosis, infertility from endometriosis, cerebral malaria, bacterial meningitis, adverse effects from amphotericin B treatment, adverse effects from interleukin-2 treatment, adverse effects from OKT3 treatment, and adverse effects from GM-CSF treatment.

3. The method of claim 1, further comprising administration of a Type IV phosphodiesterase inhibitor to said patient.

4. The method of claim 3, wherein said Type IV phosphodiesterase inhibitor is a compound having formula (II), (III), (IV), (V), (VI) or (VII):

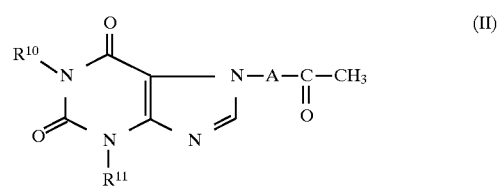

in which $R^{10}$ and $R^{11}$ are the same or different and are independently selected from the group consisting of straight-chain or branched-chain alkyl radicals with 2 to 6 carbon atoms, cyclohexyl, straight chain or branched chain alkoxyalkyl, and hydroxyalkyl radicals; and A is a hydrocarbon radical with up to 4 carbon atoms which can be substituted by a methyl group;

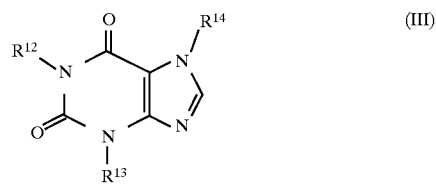

wherein at least one of $R^{12}$ and $R^{14}$ is either (a) a branched hydroxyalkyl group of the formula

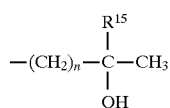

with a tertiary alcohol function, in which $R^{15}$ stands for an alkyl group with 1 to 3 carbon atoms and n stands for a whole number from 2 to 5, the other $R^{12}$ or $R^{14}$ group that may optionally be present stands for a hydrogen atom or an aliphatic hydrocarbon group $R^{16}$ with up to 6 carbon atoms, whose carbon chain may be interrupted by up to 2 oxygen atoms or may be substituted with a hydroxy or oxo group; and $R^{13}$ is an alkyl group with 1 to 4 carbon atoms; or (b) at least one of $R^{12}$ or $R^{14}$ is an oxoallyl group of the formula

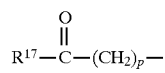

wherein $R^{17}$ is $C_1$–$C_6$ alkyl, and p=2, 3, or 4. The other $R^{12}$ or $R^{13}$ being defined as above; and $R^{13}$ represents an alkyl group with 1 to 4 carbon atoms; or (C) $R^{12}$, $R^{13}$, and $R^{14}$ are the same or different and are selected from the group consisting of (i) $C_1$–$C_6$ straight or branched chain alkyl; (ii) $C_1$–$C_6$ straight or branched chain alkoxyalkyl; (iii) $C_1$–$C_6$ straight or $C_{1-9}$ branched chain hydroxyalkyl; and in addition $R^{12}$ and $R^{13}$ can be cyclohexyl;

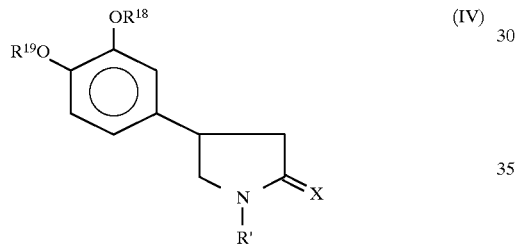
(IV)

wherein $R^{18}$ and $R^{19}$ each are alike or different and are hydrocarbon radicals having up to 18 carbon atoms with at least one being other than methyl, a heterocyclic ring, or alkyl of 1–5 carbon atoms which is substituted by one or more of halogen atoms, hydroxy, carboxy, alkoxy, alkoxycarbonyl or an amino group; amino; R' is a hydrogen atom, alkyl, aryl or acyl; and X is an oxygen atom or a sulfur atom;

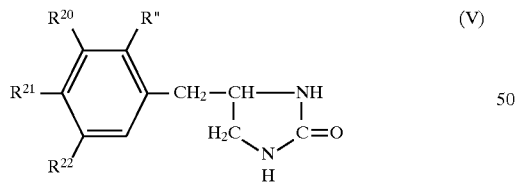
(V)

in which R" is halogen, hydrogen, $C_{1-4}$-alkyl and $C_{1-4}$ alkoxy and $R^{20}$, $R^{21}$, and $R^{22}$ taken independently of each other are hydrogen, hydroxy, $C_{1-4}$ alkoxy and hydroxy-$C_{1-4}$ alkoxy and R", $R^{20}$, $R^{21}$, or $R^{22}$ taken as an adjacent pair is alkylenedioxy;

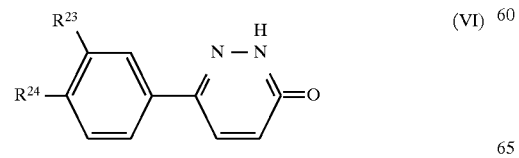
(VI)

in which one of the substituents $R^{23}$ and $R^{24}$ denotes hydrogen or C1-C4-alkoxy, and the other denotes polyfluoro-C1-C4-alkoxy;

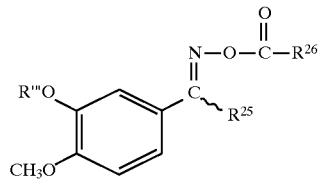
(VII)

wherein
R'" is $C_{3-7}$-alkyl, $C_{3-7}$-cycloalkyl,

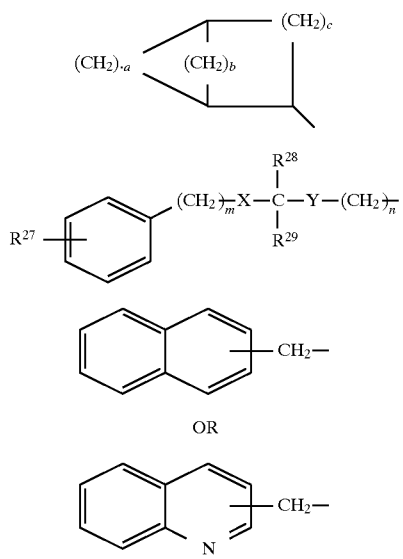

$R^{25}$ is hydrogen, lower alkyl or

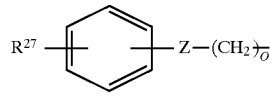

a is 1–3;

b is 1–3;

c is 0–2;

X, Y, and Z are each, independently, a bond, O, S, or NH, with the proviso that if one of X or Y is O, S, or NH, the other must be a bond;

$R^{26}$ is amino loweralkylamino, arylamino, loweralkoxy, or aryloxy;

$R^{27}$ is hydrogen, halo, hydroxy, loweralkoxy, aryloxy, loweralkanoyloxy, amino, loweralkylamino, arylamino or loweralkanoylamino;

$R^{28}$ and $R^{29}$ are each, independently hydrogen or lower alkyl;

m is 0–4;

n is 1–4; and o is 1–4.

5. The method of claim 1, wherein X is a group of the formula:

wherein n is an integer from 1–4 and Ar is a phenyl group, tolyl group, xylyl group, or mesityl group.

6. The method of claim 5, wherein n is 2 and Ar is a para-tolyl group.
7. The method of claim 1, wherein X is a group of the formula:
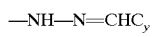
wherein $C_y$ is a $C_{3-7}$-cycloalkyl group.
8. The method of claim 3, wherein said Type IV phosphodiestearase is 4-(3-cyclopentyloxy-4-methoxyphenyl)-2-pyrrolidone.
9. The method of claim 3, wherein said $A_{2a}$ adenosine receptor agonist is SHA 211 (WRC 0474).
* * * * *